US 6,709,857 B2

(12) United States Patent
Bachur, Jr.

(10) Patent No.: US 6,709,857 B2
(45) Date of Patent: Mar. 23, 2004

(54) SYSTEM AND METHOD FOR OPTICALLY MONITORING THE CONCENTRATION OF A GAS IN A SAMPLE VIAL USING PHOTOTHERMAL SPECTROSCOPY TO DETECT SAMPLE GROWTH

(75) Inventor: Nicholas Robert Bachur, Jr., Monkton, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 310 days.

(21) Appl. No.: 09/892,012

(22) Filed: Jun. 26, 2001

(65) Prior Publication Data

US 2002/0197708 A1 Dec. 26, 2002

(51) Int. Cl.[7] .................................................. C12M 1/34
(52) U.S. Cl. .................................... 435/288.7; 435/287.5
(58) Field of Search ................................ 356/344, 432, 356/444; 374/45, 124; 422/82.05, 83; 435/287.5, 288.7

(56) References Cited

U.S. PATENT DOCUMENTS

| 4,591,272 A | * | 5/1986 | Morris et al. | ................ | 356/432 |
| 4,938,593 A | * | 7/1990 | Morris et al. | ................ | 356/344 |
| 5,926,273 A | * | 7/1999 | Kimura et al. | ............... | 356/502 |
| 6,087,181 A | * | 7/2000 | Cong | .......................... | 436/37 |
| 2003/0002038 A1 | * | 1/2003 | Mawatari | .................... | 356/300 |

* cited by examiner

Primary Examiner—David A. Redding
(74) Attorney, Agent, or Firm—Bruce S. Weintraub

(57) ABSTRACT

A system and method for monitoring the concentration of a medium in at least one container using photothermal spectroscopy. The medium can be a gas, such as oxygen or carbon dioxide, or a solid or liquid. The system and method each employs an energy emitting device, such as a laser or any other suitable type of light emitting device, which is adapted to emit a first energy signal toward a location in the container. The first energy signal has a wavelength that is substantially equal to a wavelength at which the medium absorbs the first energy signal so that absorption of the first energy signal changes a refractive index of a portion of the medium. The system and method each also employs a second energy emitting device, adapted to emit a second energy signal toward the portion of the medium while the refractive index of the portion is changed by the first energy signal, and a detector, adapted to detect a portion of the second energy signal that passes through the portion of the medium. The system and method each further employs a signal analyzer, adapted to analyze the detected portion of the second energy signal to determine an amount of a sample in the container based on a concentration of the medium in the container. In particular, the signal analyzer can analyze the detection portion of the second energy signal to determine whether the sample includes an organism which consumes or emits the medium.

14 Claims, 14 Drawing Sheets

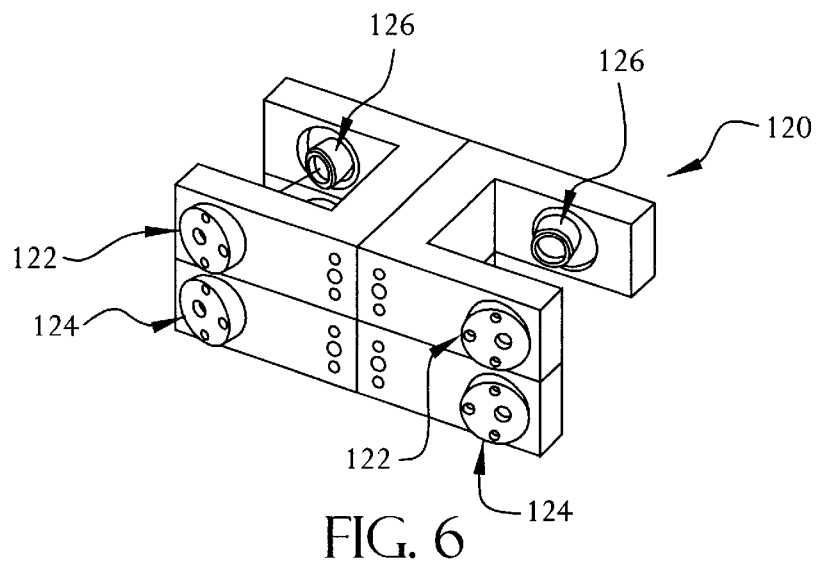
FIG. 6
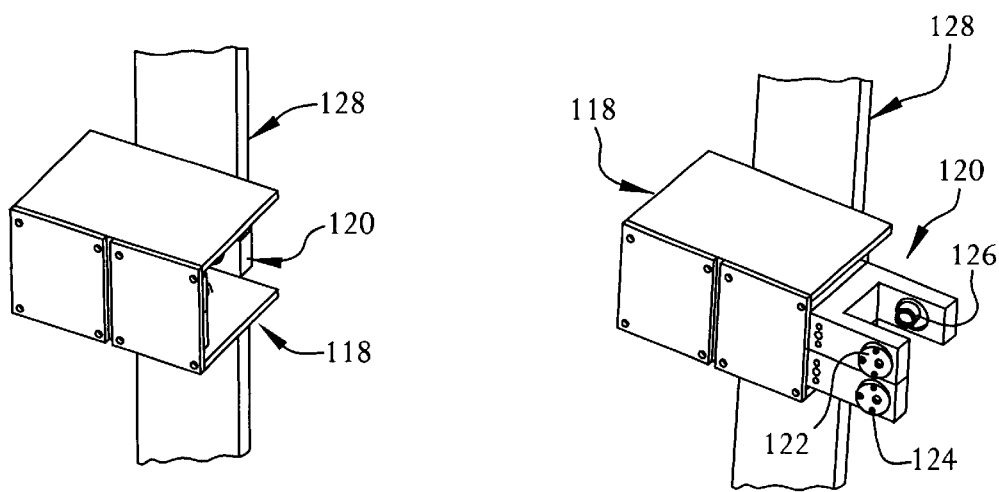
FIG. 7
FIG. 8

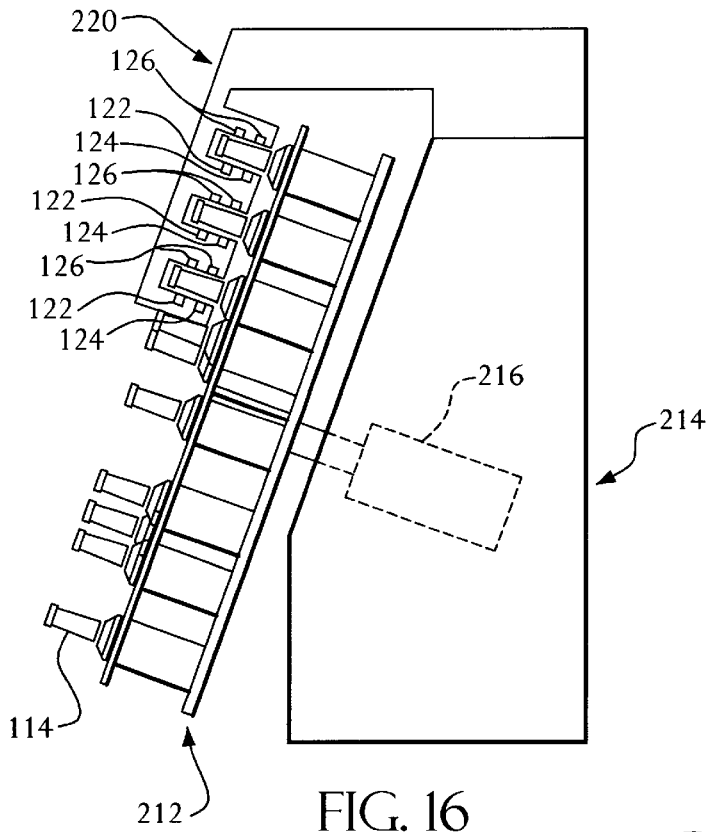
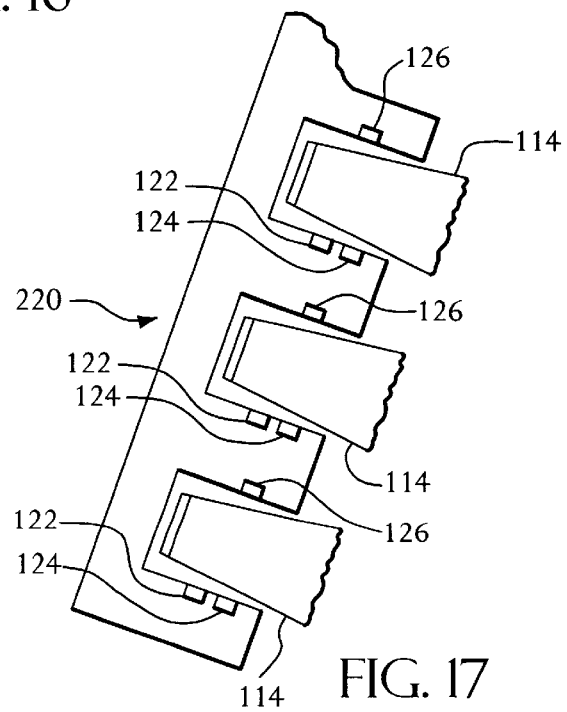
FIG. 16
FIG. 17

SYSTEM AND METHOD FOR OPTICALLY MONITORING THE CONCENTRATION OF A GAS IN A SAMPLE VIAL USING PHOTOTHERMAL SPECTROSCOPY TO DETECT SAMPLE GROWTH

CROSS-REFERENCE TO RELATED APPLICATIONS

Related subject matter is disclosed in a U.S. patent application Ser. No. 09/892,061 of Nicholas R. Bachur, Jr. et al. entitled "System and Method for Optically Monitoring the Concentration of a Gas, or the Pressure, in a Sample Vial to Detect Sample Growth" (Attorney Docket No. P-5026), the entire contents of which is incorporated herein by reference.

BACKGROUND OF THE INVENTION

1. Field of the Invention

The present invention relates to a system and method for optically monitoring the concentration of a gas in a sample vial using photothermal spectroscopy to detect the presence of sample growth. More particularly, the present invention relates to a system and method employing an excitation source, such as a diode laser, which is used to excite gas, such as carbon dioxide, in a sample vial to create a gas lens in the sample vial, and an interrogation source, such as another diode laser, which emits light through the gas lens to a detector which measures the degree that the light is refracted by the gas lens to determine the concentration of the gas in the sample vial, which is representative of microorganism growth in the sample vial.

2. Description of the Related Art

Many medical diagnoses require that a fluid sample, such as a blood sample, be taken from a patient, cultured in a growth medium, and then examined for the presence of a pathogen believed to be causing the patient's illness. The growth medium provides nutrients that allow the pathogen, such as a bacteria, virus, mycobacteria, mammalian cells or the like, to multiply to a sufficient number so that their presence can be detected.

In some cases, the pathogen can multiply to a large enough number so that it can be detected visually. For example, a portion of the culture can be placed on a microscope slide, and visually examined to detect for the presence of a pathogen of interest.

Alternatively, the presence of a pathogen or other organism can be detected indirectly by detecting for the presence of byproducts given off by the microorganism during its growth. For example, certain microorganisms such as mammalian cells, insect cells, bacteria, viruses, mycobacteria and fungi consume oxygen during their growth and life cycle. As the number of microorganisms increases in the sample culture, they naturally consume more oxygen. Furthermore, these oxygen consuming organisms typically release carbon dioxide as a metabolic byproduct. Accordingly, as the number of organisms present increases, the volume of carbon dioxide that they collectively release likewise increases.

Several methods exist for detecting the presence of carbon dioxide in a sample to determine whether organisms are present in the sample. For example, an instrument known as the Bactec® 9050 manufactured by Becton Dickinson and Company detects for the change in color of an indicator to determine whether carbon dioxide is present in a sample. That is, each sample is collected in a respective sample vial containing an indicator medium having a chemical that reacts in the presence of carbon dioxide to change color. A light sensor detects the color of the indicator medium in the sample vial when the sample vial is loaded into the instrument. If the sample contains an organism which emits carbon dioxide, the reflected or fluorescent intensity of the indicator medium will change in response to the presence of carbon dioxide. The light sensor will therefore detect this change in intensity, and the instrument will thus indicate to an operator that an organism is present in the sample contained in the sample vial. Other examples of instruments for detecting the presence of organisms in a sample by detecting for the change in carbon dioxide in the sample are described in U.S. Pat. Nos. 4,945,060, 5,164,796, 5,094,955 and 5,217,876, the entire contents of each of these patents are incorporated herein by reference.

Alternatively, instead of detecting for the presence of carbon dioxide to detect the presence of an oxygen consuming microorganism, it is possible to detect for a depletion in the concentration of oxygen in the sample of interest. In such a system, the sample vial includes an indicator whose color or fluorescence changes as the concentration of oxygen in the vial changes. This change in color or fluorescence can be detected by an instrument, which can provide an indication to a technician that oxygen in the sample is being depleted by an oxygen consuming organism within the sample. An instrument employing this oxygen detecting technique is described in U.S. Pat. No. 5,567,598, the entire contents of which are incorporated herein by reference.

The presence of oxygen consuming organisms can also be detected by detecting for a change in pressure in a sealed sample vial containing the sample of interest. That is, as oxygen in a closed sample vial is depleted by oxygen consuming organisms, the pressure in the sealed sample vial will change. The pressure will further change in the sample vial as the organisms emit carbon dioxide. Therefore, the presence of such organisms can be detected by monitoring for a change in pressure in the closed sample vial. Instruments that are capable of detecting changes in pressure in the sample vial are described in U.S. Pat. Nos. 4,152,213, 5,310,658, 5,856,175 and 5,863,752, the entire contents of each of these patents are incorporated herein by reference.

It is noted that the techniques described above each detect for the presence of oxygen or carbon dioxide in a sample vial by detecting the change in a state or condition of an indicator other than the oxygen or carbon dioxide itself. For example, certain of the techniques detect for a change in color of an indicator, while others detect for a physical change, such as the movement of a diaphragm which indicates a change in pressure. These techniques can therefore be susceptible to erroneous results if, for example, the indicators themselves are inaccurate.

Accordingly, to avoid such errors, detection probes or sensors can be inserted directly into the sample vial to detect for the presence of carbon dioxide or oxygen directly. An instrument for detecting for the presence of carbon dioxide in a sample directly is described in U.S. Pat. No. 4,971,900, the entire contents of which are incorporated herein by reference. This probe technique, however, is an invasive technique which requires that a sensor or probe be inserted directly into the sample vial containing the sample. This technique can prove hazardous because the probes can become contaminated with the organism present in the sample. Moreover, when the probes are being inserted into or removed from the vial, the potentially hazardous organisms can escape into the atmosphere, thus endangering the technician or others in the general vicinity of the instrument.

Techniques have therefore been developed which are capable of detecting the presence of, for example, carbon dioxide without the need for detecting a change in the condition of an indicator, and without the use of an invasive detector or probe. In one technique, infrared light is irradiated through the sample vial containing the sample of interest. The infrared light passing through the sample vial is detected by an infrared detector. Because carbon dioxide absorbs infrared light within a certain wavelength range, if any carbon dioxide is present in the sample vial, infrared light within that particular wavelength range will be absorbed by the carbon dioxide and thus not be detected by the infrared detector. The signals from the infrared detector are analyzed to determine whether any of the infrared light being emitted into the sample vial is absorbed and thus not detected by the infrared detector. If any absorption has occurred, the instrument provides an indication that carbon dioxide is present in the sample vial, and thus, a carbon dioxide producing organism is likely present. Examples of instruments which perform this type of technique are described in U.S. Pat. Nos. 5,155,019, 5,482,842 and 5,427,920, the entire contents of each are incorporated by reference herein.

The infrared light detecting technique has advantages over the technique described above which uses an invasive detector or probe, because the technique reduces the possibility of contamination. Furthermore, because the infrared light technique directly detects for the presence of carbon dioxide instead of detecting for a change in an indicator, more accurate results can be attained. However, the infrared light technique has certain disadvantages. For example, carbon dioxide absorbs infrared light within a somewhat wide range of wavelength, which can also be absorbed by other gases. Hence, if gases in the vial other than carbon dioxide absorb some of the infrared light, the instrument may provide a false indication that carbon dioxide is present Accordingly, the accuracy of the infrared light technique described in the patents referenced above is somewhat limited.

A need therefore exists for an improved non-invasive system and method for detecting for the presence of oxygen or carbon dioxide in a culture sample, to thus detect for the presence of an oxygen consuming or carbon dioxide producing organism in the sample.

SUMMARY OF THE INVENTION

An object of the present invention is to provide an improved system and method for optically monitoring the concentration of a gas in a sample vial to detect the presence of sample growth.

Another object of the present invention is to provide a system and method employing photothermal spectroscopy to monitor the concentration of a gas, such as oxygen or carbon dioxide, or the concentration of a liquid or solid, in the sample vial to thus detect for microorganism growth in the sample vial based on the monitored concentration.

A further object of the present invention is to provide a system and method capable of housing and incubating multiple sample vials containing respective samples, and optically monitoring the concentration of a medium in each of the sample vials by photothermal spectroscopy to detect the presence of sample growth in the vials based on the respective monitored concentrations.

These and other objects are substantially achieved by providing a system and method for monitoring the concentration of a medium in at least one container. The medium can be a gas, such as oxygen or carbon dioxide, or a solid or liquid. The system and method each employs an energy emitting device, such as a laser or any other suitable type of light emitting device, which is adapted to emit a first energy signal toward a location in the container. The first energy signal has a wavelength that is substantially equal to a wavelength at which the medium absorbs the first energy signal so that absorption of the first energy signal changes a refractive index of a portion of the medium.

The system and method each also employs a second energy emitting device, adapted to emit a second energy signal toward the portion of the medium while the refractive index of the portion or portion of an adjoining medium is changed by the first energy signal, and a detector, adapted to detect a portion of the second energy signal that passes through the portion of the medium or adjoining medium. The system and method each further employs a signal analyzer, adapted to analyze the detected portion of the second energy signal to determine an amount of a sample in the container based on a concentration of the medium in the container. In particular, the signal analyzer can analyze the detection portion of the second energy signal to determine whether the sample includes an organism which consumes or emits the medium.

BRIEF DESCRIPTION OF THE DRAWINGS

These and other objects, advantages and novel features of the invention will be more readily appreciated from the following detailed description when read in conjunction with the accompanying drawings, in which:

FIG. 6 is a detailed view of an example of a sensor head assembly employed in the monitoring assembly shown in FIGS. 4 and 5;

FIG. 7 is a detailed view illustrating the sensor head assembly shown in FIG. 6 retracted into the sensor head housing of the movable monitoring assembly shown in FIGS. 4 and 5;

FIG. 8 is a detailed view showing the sensor head assembly shown in FIG. 6 extended from another end of the sensor head housing of the monitoring assembly shown in FIGS. 4 and 5;

FIG. 16 is a side view of the carousel and detector head arrangement shown in FIG. 15; and FIG. 17 is a detailed view of the detector assembly arrangement as shown in FIGS. 15 and 16.

DETAILED DESCRIPTION OF THE PREFERRED EMBODIMENTS

Figure 1:
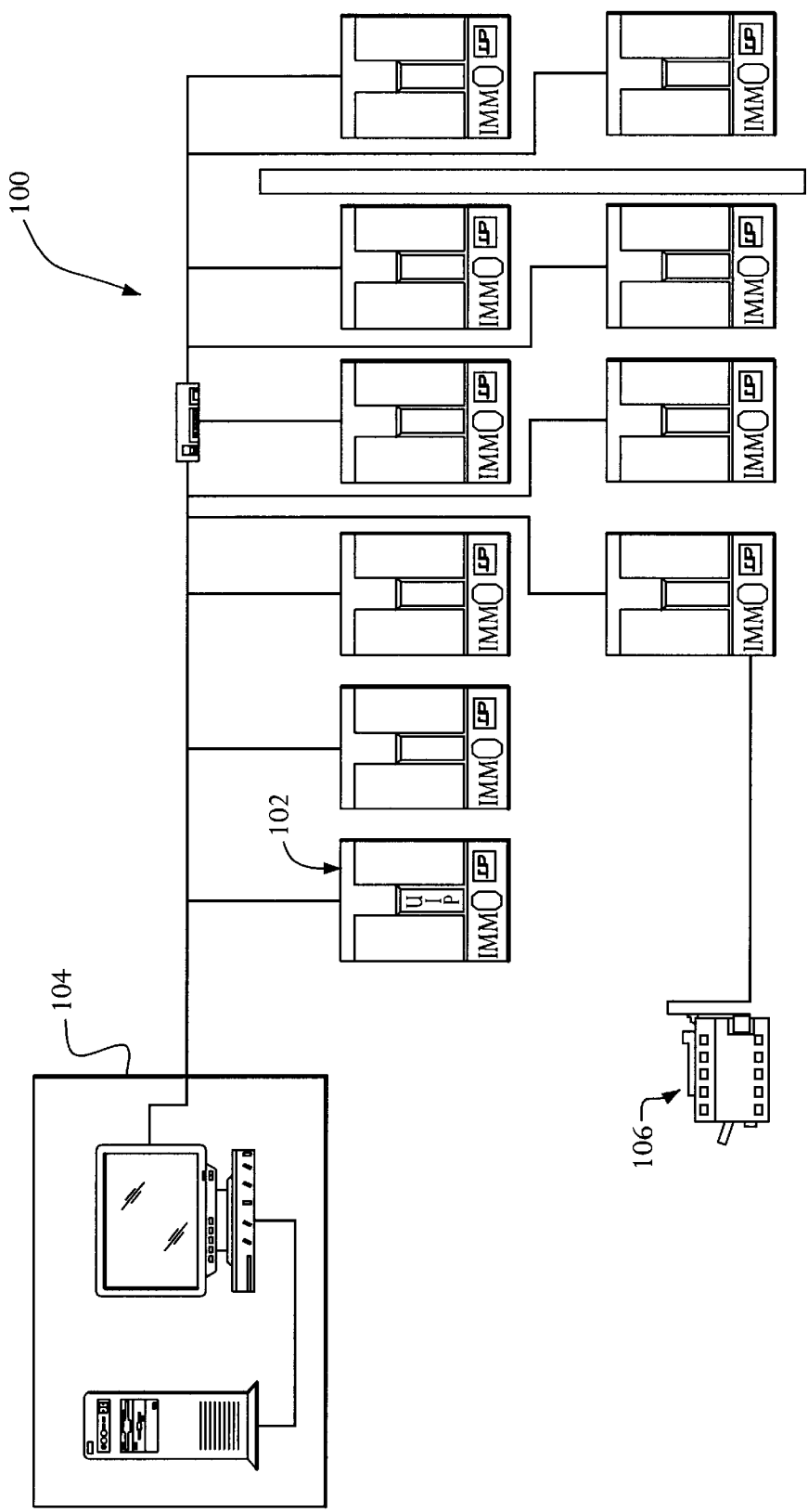
FIG. 1 is a block diagram of a system employing multiple incubation and measurement instruments according to an embodiment of the present invention, which each uses photothermal spectroscopy to monitor the concentration of a gas, such as oxygen or carbon dioxide, in sample vials, to thus detect for microorganism growth in the sample vials.

A system 100 for detecting growth of microorganisms in sample cultures according to an embodiment of the present invention is shown in FIG. 1. As illustrated, the system 100 includes a plurality of incubation and measurement modules 102 that are connected to a central computer 104. The central computer 104 can control the incubation temperatures and times, as well as the timing of the measurements performed by the modules 102, and can collect and classify the data readings obtained by the modules 102. The system 100 can also include a data output device, such as a printer 106, that can be controlled by the central computer 104 to print data readings obtained by the incubation and measurements modules 102.

Figure 2:
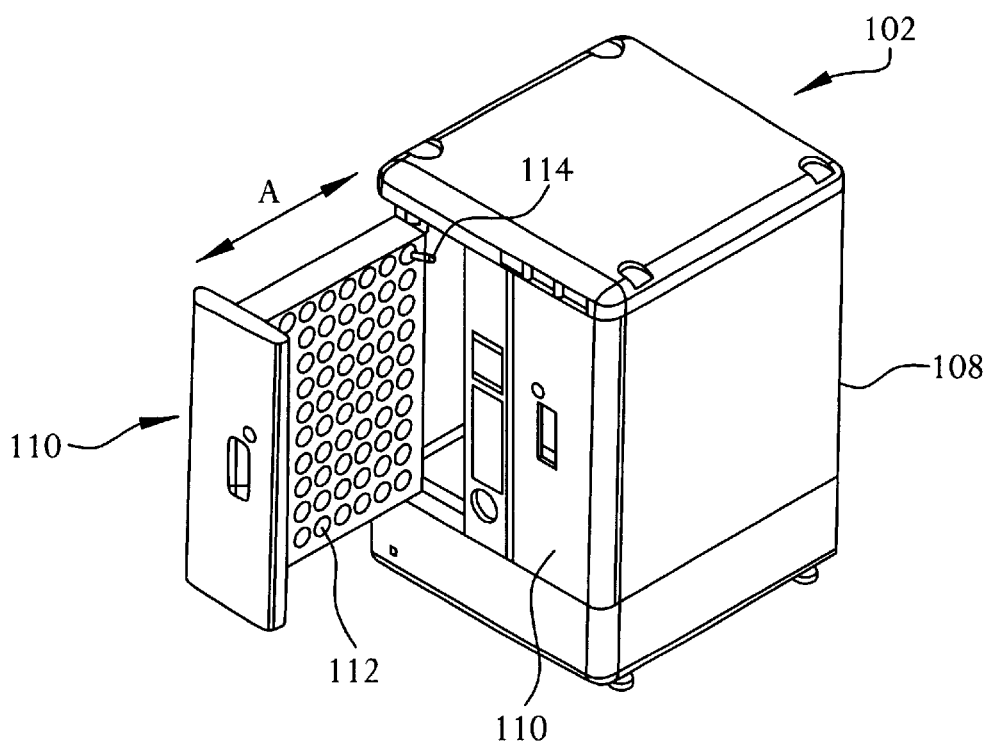
FIG. 2 is a detailed view of an instrument employed in the system shown in FIG. 1.
Figure 3:
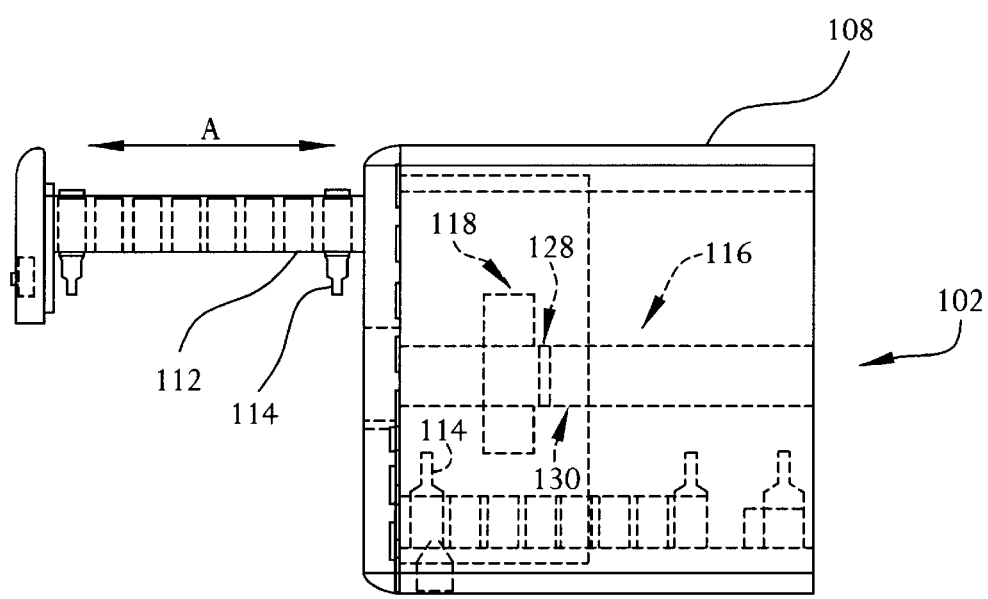
FIG. 3 is a top view of the instrument shown in FIG. 2.
Figure 4:
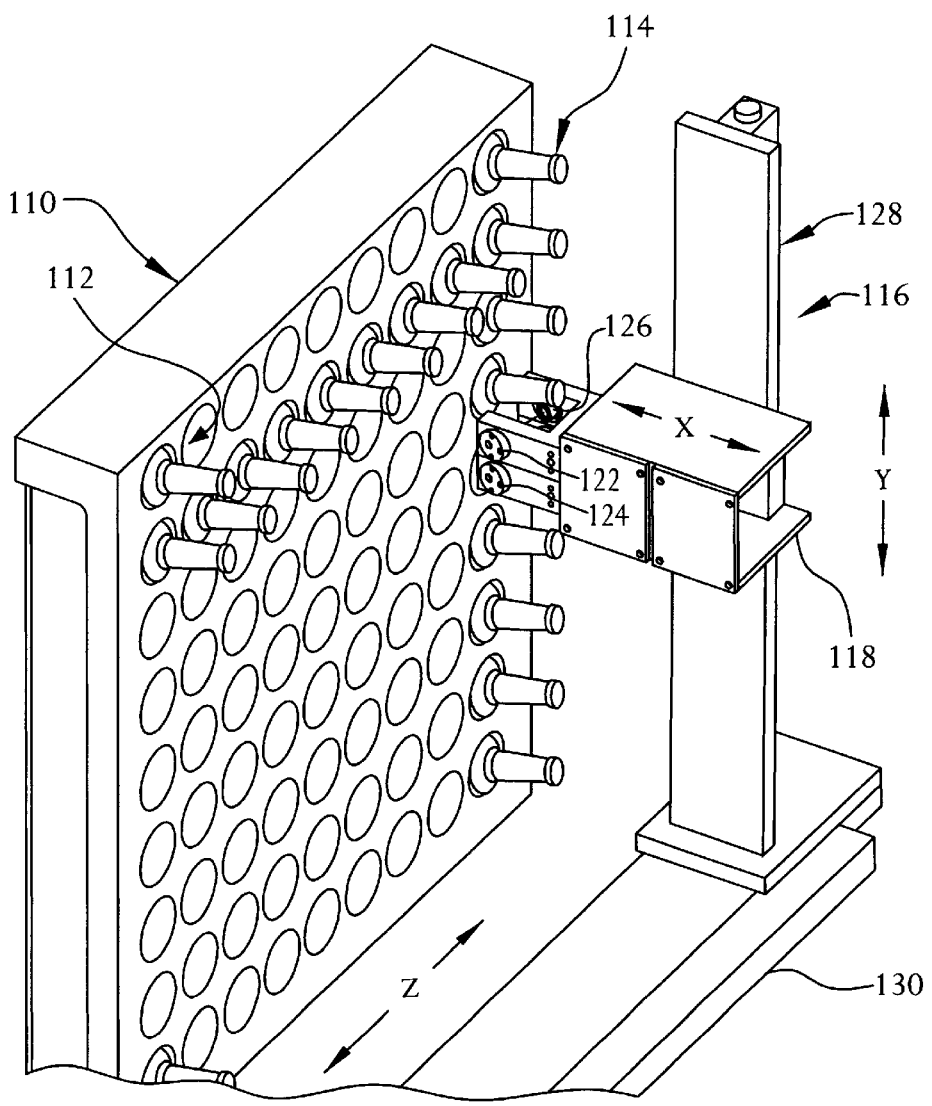
FIG. 4 is a detailed view of an example of a movable monitoring assembly employed in the instrument shown in FIGS. 1–3 which uses photothermal spectroscopy techniques to monitor the concentration of a gas in the sample vials.
Figure 5:
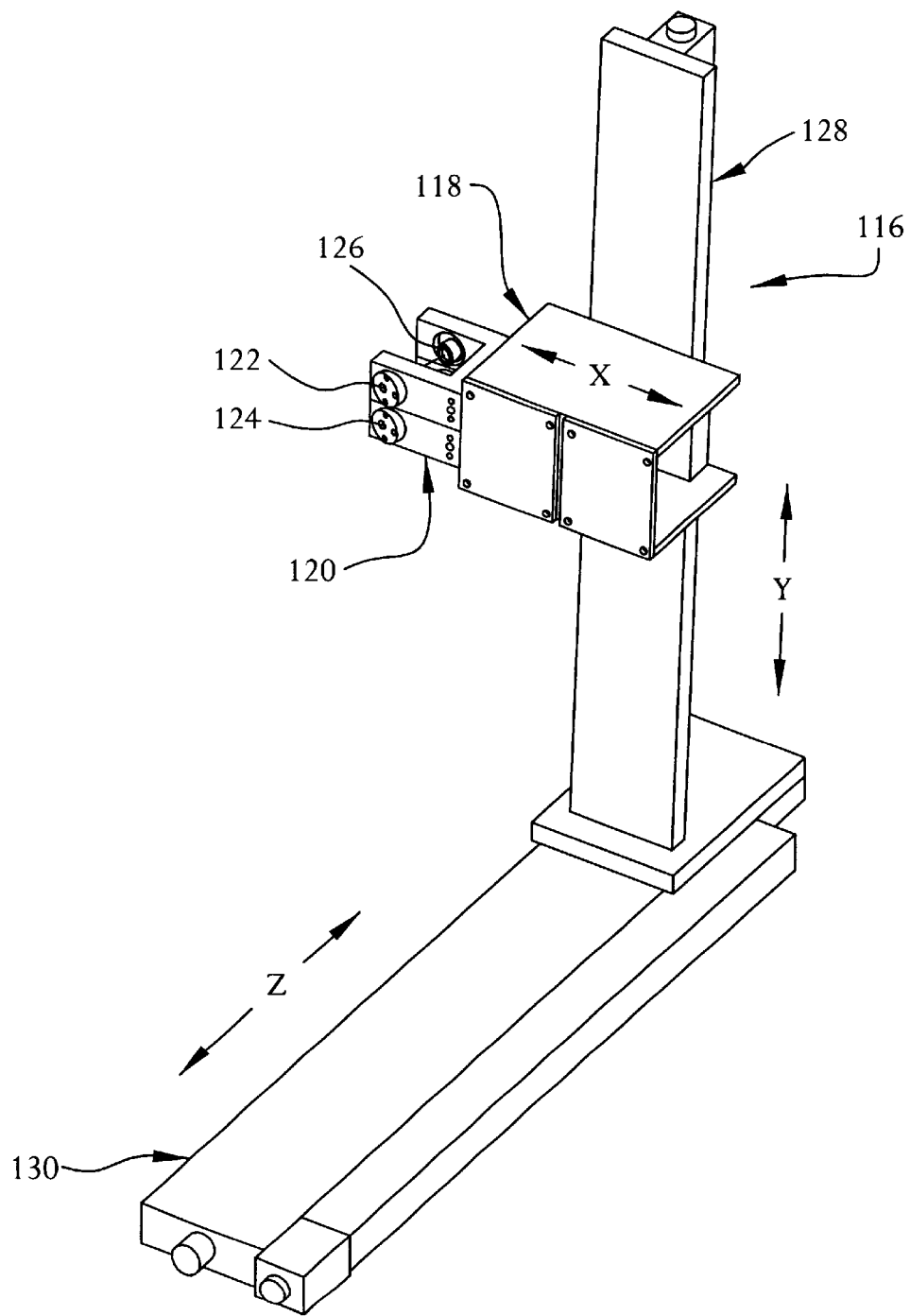
FIG. 5 is another view of the monitoring assembly shown in FIG. 4.

Further details of the incubation and measurement modules 102 are shown in FIGS. 2 and 3. As illustrated, each incubation and measurement module 102 in this example includes a housing 108 and two shelves 110 that can be slid into and out of the housing 108 in a direction along arrow A. Each shelf 110 includes a plurality of openings 112, each of which is adapted to receive a sample vial 114. The openings 112 are arranged in a plurality of rows and columns as shown, and each shelf 110 can have any practical number of openings. For example, the openings 112 can be arranged in nine rows, with nine columns in each row, thus totaling 81 openings 112 per shelf 110.

When a sample culture is to be analyzed by the incubation and measurement module 102, the sample culture is placed in a sample vial 114, and the sample vial 114 is loaded into a respective opening 112 in the incubation and measurement module 102. The sample vial 114 is a closed sample vial in this example. The incubation and measurement module 102 can further include a keyboard, a barcode reader, or any other suitable interface that enables a technician to enter information pertaining to the sample into a database stored in a memory in the incubation and measurement module 102, in the central computer 104, or both. The information can include, for example, patient information, sample type, the row and column of the opening 112 into which the sample vial 114 is being loaded, and so on.

Each incubation and measurement module 102 further includes a movable monitoring assembly 116 which is capable of monitoring the contents of a medium in the sample vials 114 through the use of a technique known as photothermal spectroscopy. The principles of photothermal spectroscopy are generally described in a publication by Stephen E. Bialkowski entitled "Photothermal Spectroscopy Methods for Chemical Analysis", John Wiley & Sons, Inc., 1996, the entire content of which is incorporated by reference herein.

Details of the movable monitoring assembly 116 will now be described with reference to FIGS. 4–9. As shown, the monitoring assembly 116 includes a sensor head housing 118 which houses a sensor assembly 120 that includes a plurality of lasers 122 and 124 and a detector 126, the details of which are described below.

Sensor head housing 118 is movably mounted to a vertical shaft 128 and can be moved in the "Y" direction along the vertical shaft 128 by, for example, a motor and pulley arrangement (not shown) or any other type of arrangement as can be appreciated by one skilled in the art. As further illustrated, vertical shaft 128 is movably mounted to a horizontal shaft 130, and can be moved along the "Z" direction along horizontal shaft 130 by a motor or pulley assembly (not shown) or any other type of arrangement as can be appreciated by one skilled in the art. As shown in FIG. 3, monitoring assembly 116 can be mounted in a module 102 between the two shelves 110 so that the sensor assembly 120 can take readings from sample vials 114 in both shelves 110 as described in more detail below.

As further shown in more detail in FIGS. 7 and 8, the sensor assembly 120 is movably mounted in sensor head housing 118 so that sensor assembly 120 can be retracted into the sensor head housing 118 along the "X" axis by a motor and gear or pulley arrangement (not shown), or by any other type of arrangement as can be appreciated by one skilled in the art. As shown in FIG. 8, the sensor assembly 120 can be further moved along the "X" direction to extend out of the other side of sensor head housing 118.

The operation of monitoring assembly 116 will now be described with reference to FIGS. 3–9. As discussed briefly above, central controller 104 (see FIG. 1) or a controller (not shown) in module 102 can control movement of the sensor head housing 118 and vertical shaft 128, as well as the extension of the sensor assembly 120, so that one pair of lasers 122 and 124 and one detector 126 are positioned on opposite sides of the neck of a sample vial 114 of interest loaded into an opening 112 in one of the shelves 110, as shown conceptually in FIG. 9. In this example, laser 122 is a diode laser that emits photons (an excitation laser beam) having a wavelength at or about 2004 nanometers, which is in the absorbance wavelength band for carbon dioxide. The laser 122 is energized by a reference voltage source 132 and an alternating voltage source 134 as shown, under the control of, for example, central controller 104 or a controller in module 102.

When a photon emitted from laser 122 strikes a carbon dioxide molecule and is absorbed by the carbon dioxide molecule, thermal energy is released into the surrounding atmosphere in the vial 114. The thermal energy heats the gas molecules in the vicinity of the carbon dioxide molecule, and the local air density is reduced. As this density is reduced, the refractive index $n_D$ of the atmosphere in the vial 114 consequently is reduced. This localized reduction in the refractive index $n_D$ of the atmosphere in the neck of vial 114 creates a gas lens 136 that is capable of refracting light.

While laser 122 is energized to form the gas lens 136 in the neck of vial 114, second laser 124 is energized by a voltage source 138 under the control of, for example, central controller 104 or a controller in module 102. In this example, laser 124 is a diode laser that emits photons (an interrogation laser beam) at a wavelength at or about 650 nanometers. The photons are directed toward the intersection of the excitation laser beam emitted from excitation laser 122 and the gas contained in the neck of vial 114 as shown. As the interrogation laser beam emitted from laser 124 strikes the gas lens 136 formed by the photothermal effect described above, the interrogation laser beam is defocused or refracted by the gas lens 136. It is noted that as the concentration of carbon dioxide in the gas mixture increases, the gas lens 136 formed will have a greater refractive effect on the interrogation laser beam. That is, a small concentration of carbon dioxide will form a lens 136 having a smaller refractive effect and thus, the interrogation laser beam will be refracted less. However, a large concentration of carbon dioxide will form a lens 136 having a larger refractive effect and thus, the interrogation laser beam will be refracted more. Improvements to the interrogation beam path not shown in the figures such as optical lenses or spatial filtering may be applied to increase the magnitude of the gas lens' refractive effect.

Figure 9:
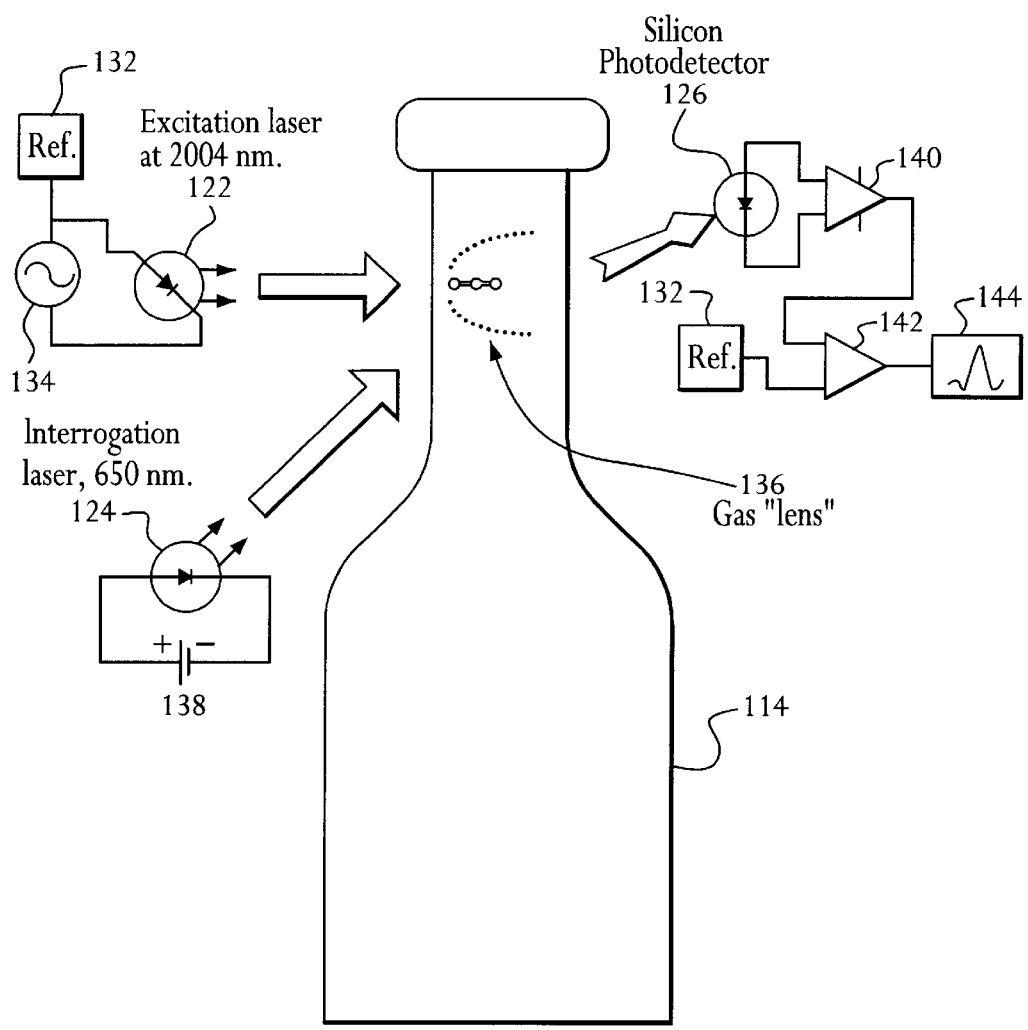
FIG. 9 is a conceptual block diagram of an example of electronic components used by the monitoring assembly to monitor the concentration of one or more gasses in the sample vials.

As further shown in FIG. 9, detector 126, which in this example is a silicon photodetector, receives the refracted interrogation laser beam that has passed through gas lens 136. The photocurrent output by detector 126 is input to a transimpedance amplifier 140, and the output of amplifier 140 is input to a lock-in amplifier 142. A reference voltage provided by reference voltage source 132, which is representative of the modulation waveform of the excitation laser 122, is also input to the lock-in amplifier 142, which is capable of accommodating relatively poor signal to noise ratios for the detected refracted interrogation laser beam. The output of the lock-in amplifier 142 can be provided to a display 144, that displays a waveform which is representative of the concentration of carbon dioxide in the vial 114. The waveform can be further analyzed to determine the amount of sample growth in the vial 114, which in this example is proportional to the concentration of carbon dioxide in the vial 114. Also, it is noted that other signal processing techniques, such as those employing discriminator circuits, ratio detectors, phase shift demodulation, and so on, can be used to process the photocurrent output by detector 126.

The sensor head housing 118 can then be moved along the "Y" direction to take readings from that column of sample vials 114 in the manner described above. The sensor assembly 120 can then be retracted into the sensor head housing 118 as shown in FIG. 7 so that the vertical shaft 128 and sensor head housing 118 can be moved in the "Z" direction to be aligned with another column of sample vials 114. The reading process can then be repeated to take readings from that column of sample vials 114, and the retracting, moving and reading process can be repeated for all columns of sample vials 114.

Once readings have been taken from all of the sample vials 114 in all of the columns in shelf 110, the central controller 104, for example, or a controller in the module 102, can control the monitoring assembly 116 to take readings from the sample vials 114 in the opposite shelf 110 in a similar manner. In this event, the central controller 104 or other controller controls the monitoring assembly 116 to position the sensor head housing 118 for reading a column of sample vials 114 in that shelf 110. Once the sensor head housing 118 has been properly positioned, the sensor head housing 118 is controlled to extend the sensor assembly 120 from the opposite end of the sensor head housing 118 as shown in FIG. 8. The central controller 102 or other controller then controls the sensor head housing 118 to move along the vertical shaft 128 so that the sensor assembly 120 can take readings from all the sample vials 114 in that column in a manner similar to that described above.

Once all of the sample vials 114 in that column have been read, the sensor head housing 118 is controlled to retract the sensor assembly 120 as shown in FIG. 7. The central controller 104 or other controller then controls movement of the vertical shaft 128 and sensor head housing 118 in the "Z" direction along horizontal shaft 130 until the sensor head housing 118 is positioned to read another column of sample vials 114. The sensor head housing 118 is then moved in the "Y" direction along vertical shaft 128 as appropriate to take readings from the sample vials 114 that occupy column of sample vials 114. The process is then repeated until readings have been taken from the sample vials 114 in all of the columns of that second shelf 110. Once all of the readings have been taken, or in contemporaneously, the data can be processed, displayed and analyzed in a manner discussed above.

The photothermal spectroscopy technique described above has several advantages over other types of spectroscopy techniques used to monitor gas metabolites as a representation of sample growth. For example, the photothermal spectroscopy technique described above has a sensitivity of 1000 to 10,000 times that of gas absorption spectroscopy. Also, with the photothermal spectroscopy technique, the sensitivity of the measurements tends to increase as the volume of sample gas decreases. On the contrary, with the gas absorption spectroscopy technique, the sensitivity of the measurements increase with increased gas volume and decrease with decreased gas volume. Accordingly, the photothermal spectroscopy technique is more desirable for use in monitoring samples that produce small volumes of metabolites.

In addition, the photothermal spectroscopy technique described above can be used to interrogate liquids and solids using the excitation laser 122 and interrogation laser 124, and the detector 126, and the material being interrogated need not be transparent. Furthermore, the excitation laser 122 need not be a laser, but rather, can be any type of light source that is capable of emitting light having a wavelength confined to the absorption band of the gas being analyzed (e.g., carbon dioxide). However, the light source must not emit light that has a wavelength within the absorption bands of other gases that may be present in the atmosphere in which the gas being analyzed is present. In other words, for the above example, the excitation light source 122 must not emit light having a wavelength that is within the absorption band of any gases other than carbon dioxide that may also be present in the neck of vial 114. For example, the light source 122 can be an LED that produces light throughout the absorption spectrum of the gas under analysis (e.g., carbon dioxide) can be used. Alternatively, a strobe lamp can be used in conjunction with narrow band absorption filters which confine the wavelength of the light entering the neck of the sample vial 114 to the absorption band of carbon dioxide or any other gas or medium being analyzed. Also, a tunable bandpass filter can be applied to the path of the excitation light emitted from excitation light source 122 to permit rapid scanning of many different types of analytes over a wide wavelength range.

It is also noted that the interrogation laser 124 can be an inexpensive type of laser, such as the type used in laser pointers. Furthermore, the detector 126 can be a photodiode detector using an inexpensive silicon material capable of detecting light in the visual wavelength range rather than, for example, expensive Aluminum Gallium Arsenide Phosphide detectors that are typically used to detect light in the mid-infrared (mid-IR) range.

It is further noted that the photothermal spectroscopy techniques described above can be used to analyze molecules other than carbon dioxide. For example, the monitoring assembly 116 can be used to monitor the concentration of oxygen ($O_2$), $NH_3$, $H_2S$, $CH_4$ or $SO_2$, in the head space above a liquid growth medium in the sample vials 114 to detect a microorganisms' metabolic activity. However, to detect these different molecules, the excitation laser or light source 122 needs to be configured to emit light within the absorption band of the molecules of interest. For example, to detect $NH_3$, a laser 122 that emits light in the 1997 nanometer band is used. To detect $H_2S$, a laser 122 that emits light in the 1570 nanometer band is used, to detect $CH_4$, a laser 122 that emits light in the 1650 nanometer band is used, and to detect $SO_2$, a laser that emits light in the 7280 nanometer band is used. The monitoring assembly 116 can also be used to monitor the concentration of other molecules such as glucose, creatine kinase-MB, and so on.

Figure 10:
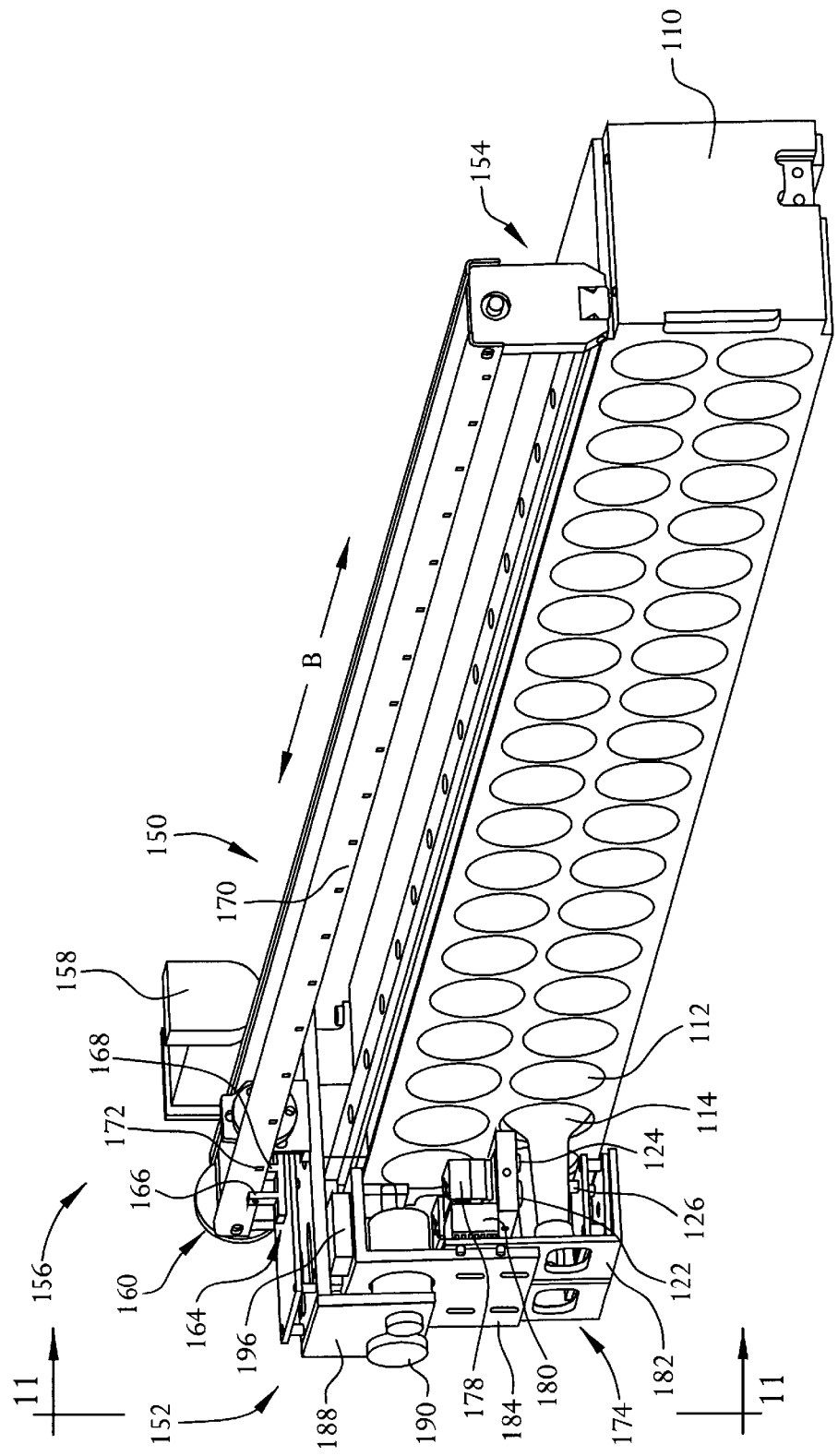
FIG. 10 is a block diagram of an example of another type of monitoring assembly that can be employed in the instrument shown in FIGS. 2 and 3.
Figure 11:
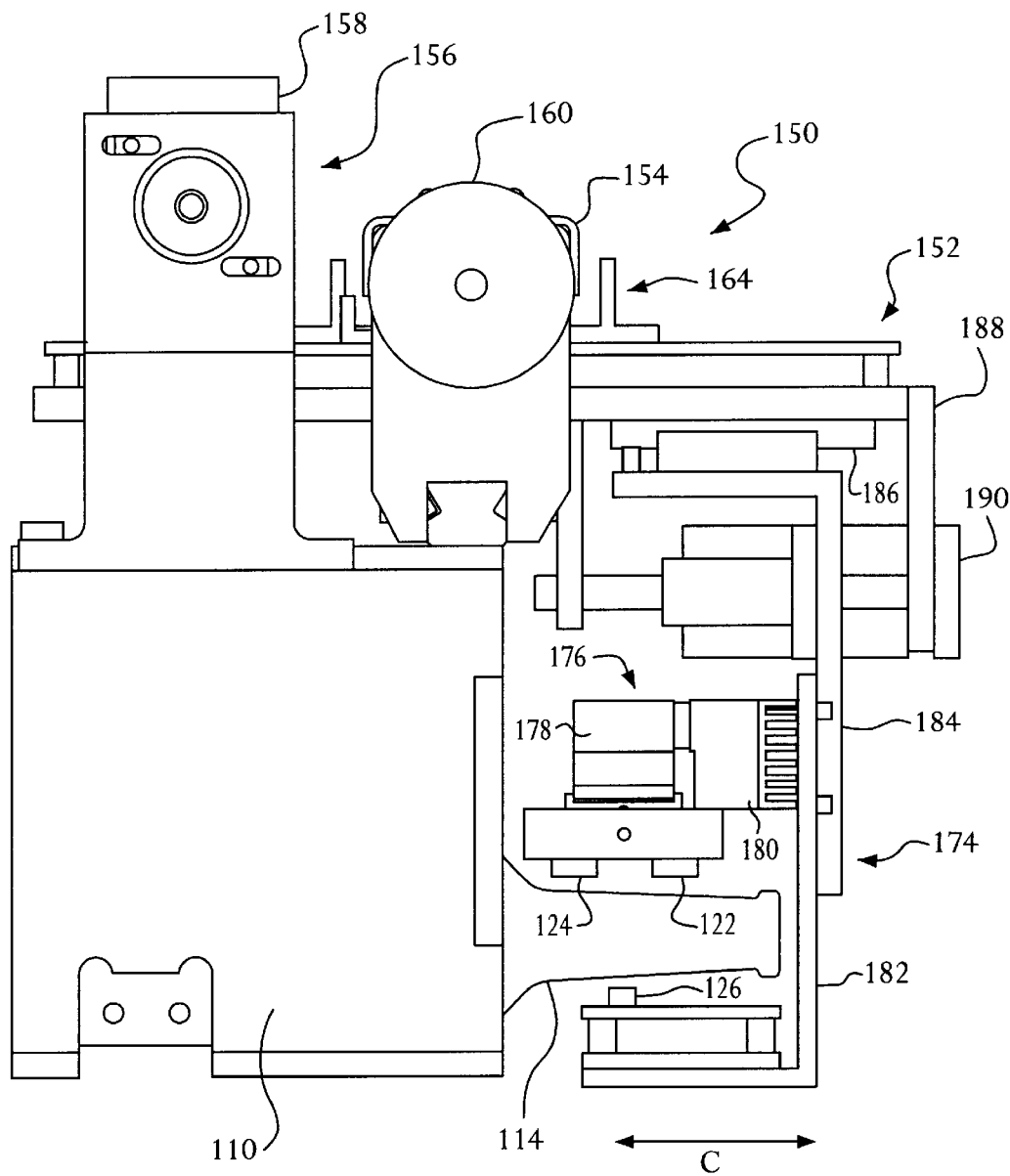
FIG. 11 is another block diagram of the monitoring assembly shown in FIG. 10.
Figure 12:
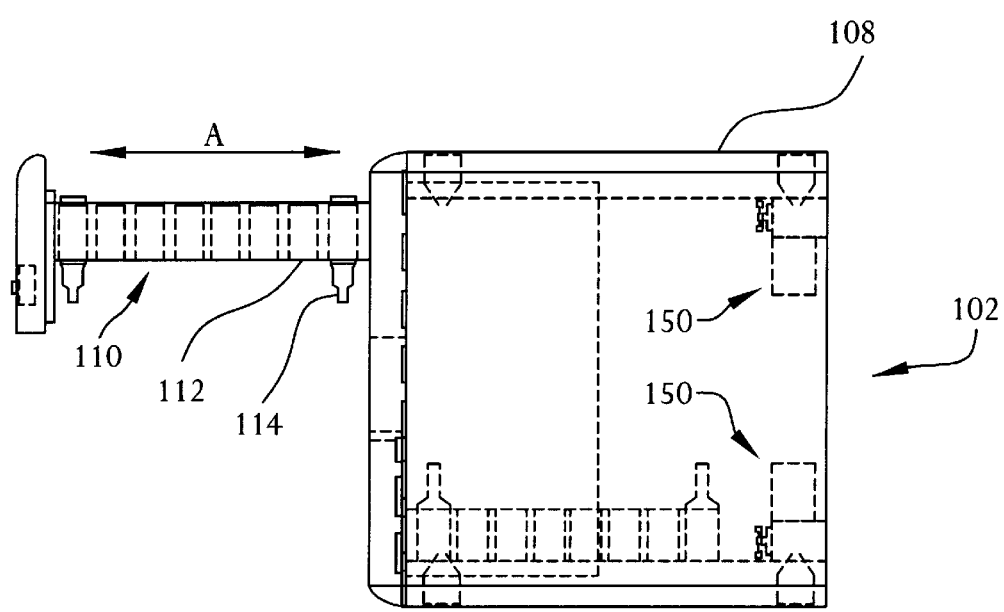
FIG. 12 is a top view of the instrument shown in FIG. 2 including the monitoring assembly shown in FIGS. 10 and 11.
Figure 13:
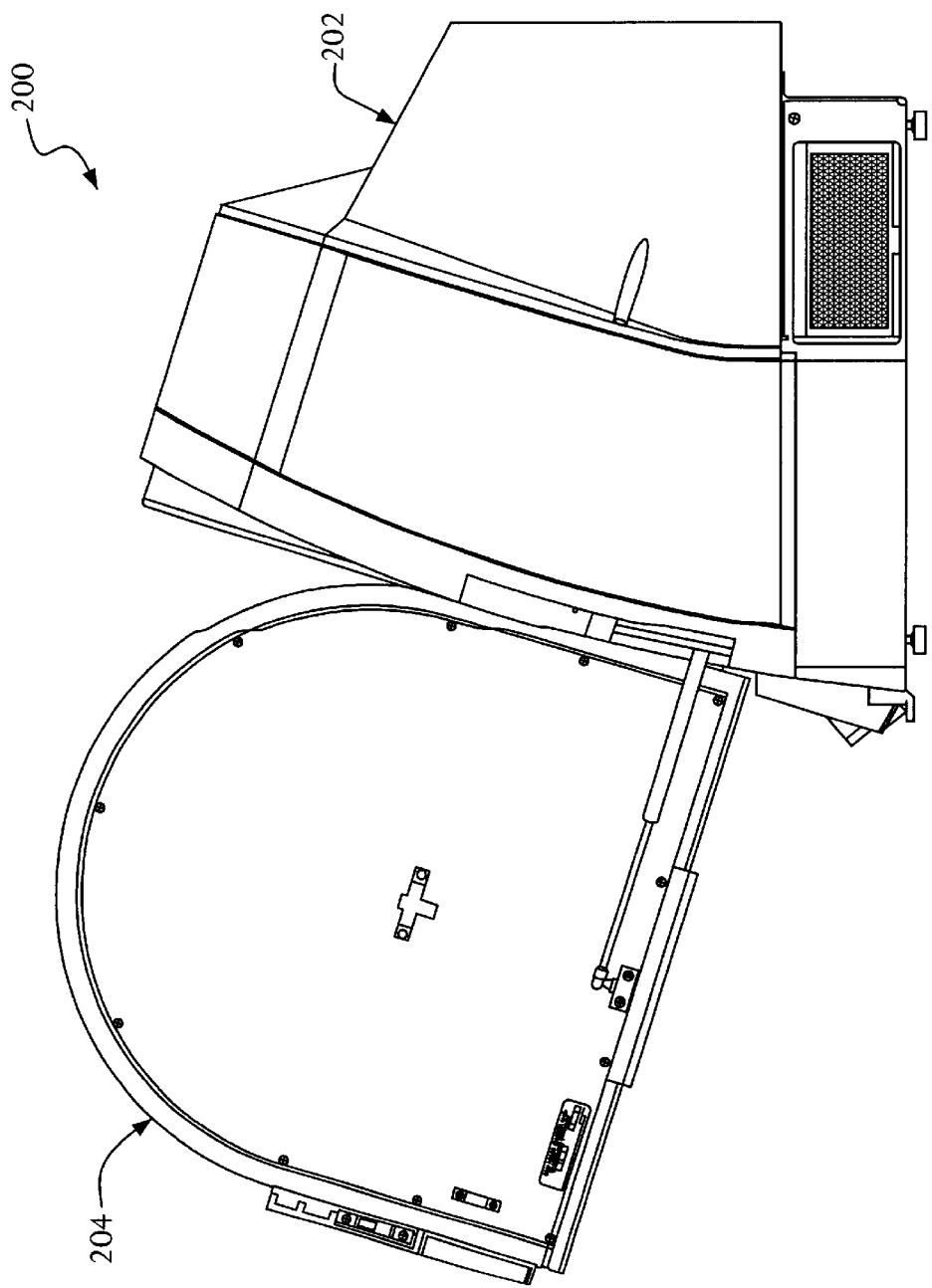
FIG. 13 is a side view of another type of instrument employing another embodiment of a detector assembly which uses infrared laser spectrography and dual wavelength modulation techniques to monitor the concentration of a gas or the pressure in sample vials according to another embodiment of the present invention.

In addition, the monitoring assembly 116 can have different configurations. For example, as shown in FIGS. 10–12, the incubation and measurement module 102 can be configured to include a plurality of monitoring assemblies 150, which are positioned in the incubation and measurement modules 102 to obtain readings from the sample vials 114. In the example shown in FIGS. 10 and 11, each monitoring assembly 150 is configured to obtain measurements from sample vials 114 inserted in two rows of openings 112. However, the monitoring assembly 150 can be configured to obtain readings from sample vial 114 in any number of rows of openings 112 as desired.

The monitoring assembly 150 includes a movable assembly 152 which, in this example, is slidably coupled to a rail assembly 154 which is fixedly coupled to the top portion of shelf 110. A motor and pulley assembly 156 comprising a motor 158, such as a D.C. servo motor, and a pulley arrangement 160 that is driven by the motor 158, is coupled to the rail assembly 154 and movable assembly 152. The motor 158 is controlled by, for example, central computer 104 or a computer in incubation and measurement module 102 to drive the pulley arrangement 160 which, in response, drives movable assembly 152 to slide along rail assembly 154 in a sample vial reading direction indicated by arrow B in FIG. 10.

Moveable assembly 152 also includes a sensor 164 which includes a light emitting device 166 and a detector 168 positioned on opposite sides of a rail 170 of rail assembly 154. As the motor and pulley assembly 156 drives the moveable assembly 152 along rail assembly 154, the sensor 164 detects the openings 172 in the rail 170, and provides a signal indicative of this detection to central computer 104 or a computer in the incubation and measurement module 102. The central computer 104 or a computer in the incubation and measurement module 102 uses this detection signal to monitor the position of the moveable assembly 152 along rail assembly 154. Also, because each opening 172 corresponds to a respective column of openings 112 in the shelf 110, the computer can determine which sample vials 114 are being read by the detectors in the moveable assembly 152 of monitoring assembly 150.

Moveable assembly 152 further includes a plurality of sensor assemblies 174, the number of which corresponds to the number of rows of sample vials 114 that the monitoring assembly 150 is configured to read. That is, if the monitoring assembly 150 is configured to read two rows of sample vials 114, the movable assembly 118 will include two sensor assemblies 174. For illustration purposes, FIGS. 10 and 11 show only one sensor assembly 174. Like sensor assembly 118 described above, each sensor assembly 174 includes an excitation laser or light emitting device 122, and an interrogation laser or light emitting device 124, as described above. The laser 122 can be coupled to a laser assembly 176, which includes a cooling and heating device 178 that can cool or heat the laser 122 to tune the frequency of the light being emitted by the laser 122. In other words, because the laser 122 emits light having a single frequency, central computer 104 or another controller can control the cooling and heating device 178 to change these frequencies, thus enabling the laser 122 to scan a range of frequencies. The laser assembly 176 further includes a heat sink 180 that can dissipate heat from the cooling and heating device 178, and thus aid in controlling the temperature of the laser 122. A similarly configured cooling and heating device 178 and heat sink 180 can be employed in the laser assembly 120 described above (see FIGS. 4–8) to heat and cool laser 122 in that laser assembly as desired.

As further illustrated, each sensor assembly 174 includes a detector 126 that is mounted to receive the laser light being emitted by laser 124 that has passed through the gas lens 136 that has been created by the light from the excitation laser 122 as described above. The lasers 122 and 124, laser assembly 176, and detector 126 are coupled to a laser and detector mounting bracket 182, that is further coupled to a movable mounting bracket 184. The movable mounting bracket 184 is coupled along slide rails 186 to a fixed mounting bracket 188, which is coupled to rail assembly 154 for movement along rail assembly 154 by motor and pulley assembly 156. A motor 190 is coupled to movable mounting bracket 184 and is controlled by central computer 104 or a computer in the incubation and measurement module 102 to move the movable mounting bracket 184 in a direction along arrow C as shown in FIG. 11. The motor 190 can thus position lasers 122 and 124 and detector 126 at the appropriate location along the neck of sample vial 114 to obtain the most accurate readings. Also, as can be appreciated from the above description, by moving the fixed mounting bracket 188 along rail assembly 154, the motor and pulley assembly 156 translates the entire movable assembly 152 including the lasers 122 and 124 and detector 126 along the direction B in FIG. 10. This movement thus positions the lasers 122 and 124 and detector 126 at the necks of the sample vials 114 in the row of sample vials 114, so that readings can be taken from all the sample vials 114 in the row.

It is further noted that the techniques described above are not limited to use with a particular type of sample vial. Rather, sample vial 114 can by any of the various types of culture vessels capable of containing the growth media. The sample vials 114 also can use various types of growth media to allow for detection and observation of the growth of mammalian cells, insect cells, bacteria, virus, mycobacteria, fungi, and other organisms which produce or consume gases as part of their growth and life cycle. The sample vials 114 can include a gas permeable membrane, slug, aliquot, or target which permits the optical interrogation of the gas signal and excludes intervening liquids or solids.

The above carbon dioxide, oxygen and other gas detection techniques can also be used to test if materials which are designed to be sterile are indeed free of contamination or infection with any of the organisms listed above. Examples of materials which may be tested includes processed foods, biological preparations such as banked human blood, mammalian cell lines and prepared injectables.

The photothermal spectroscopy described above for the detection of carbon dioxide and oxygen, as well as other gases, can also be used to enhance growth detection, provide presumptive speciation, and to separate background metabolism such as that caused by blood cells from bacterial or other cells. The techniques described above could also be used to determine the quantity of oxygen, carbon dioxide gas or other gases flushed into sealed containers as a preservative or stabilizer to maintain a product's shelf life or quality, or to detect immediate gas concentrations within a gas stream used, for example, in a production supply line.

In the arrangements discussed above, the light emitting devices and sensors move with respect to the containers. However, it is noted that the apparatus can be configured so that the containers are housed in a rotor, drum, conveyor or the like and controlled to move past the light emitting devices and sensors which remain stationary. In this arrangement, the containers are thus sensed as they move between the light emitting devices and sensors, and the readings obtained representing the contents of the containers are evaluated in the manners described above.

That is, as shown in FIGS. 13–17, an instrument 200 can employ a stationary monitoring assembly as will now be described. Specifically, instrument 200 includes a housing 202 and a door 204 that is coupled to the housing 202 by a hinge 206 and a piston arrangement 208 to provide access to the interior chamber of the housing 202. As discussed above with regard to a module 102, instrument 200 can act as an incubation chamber to incubate the samples stored in the sample vials 114.

Figure 14:
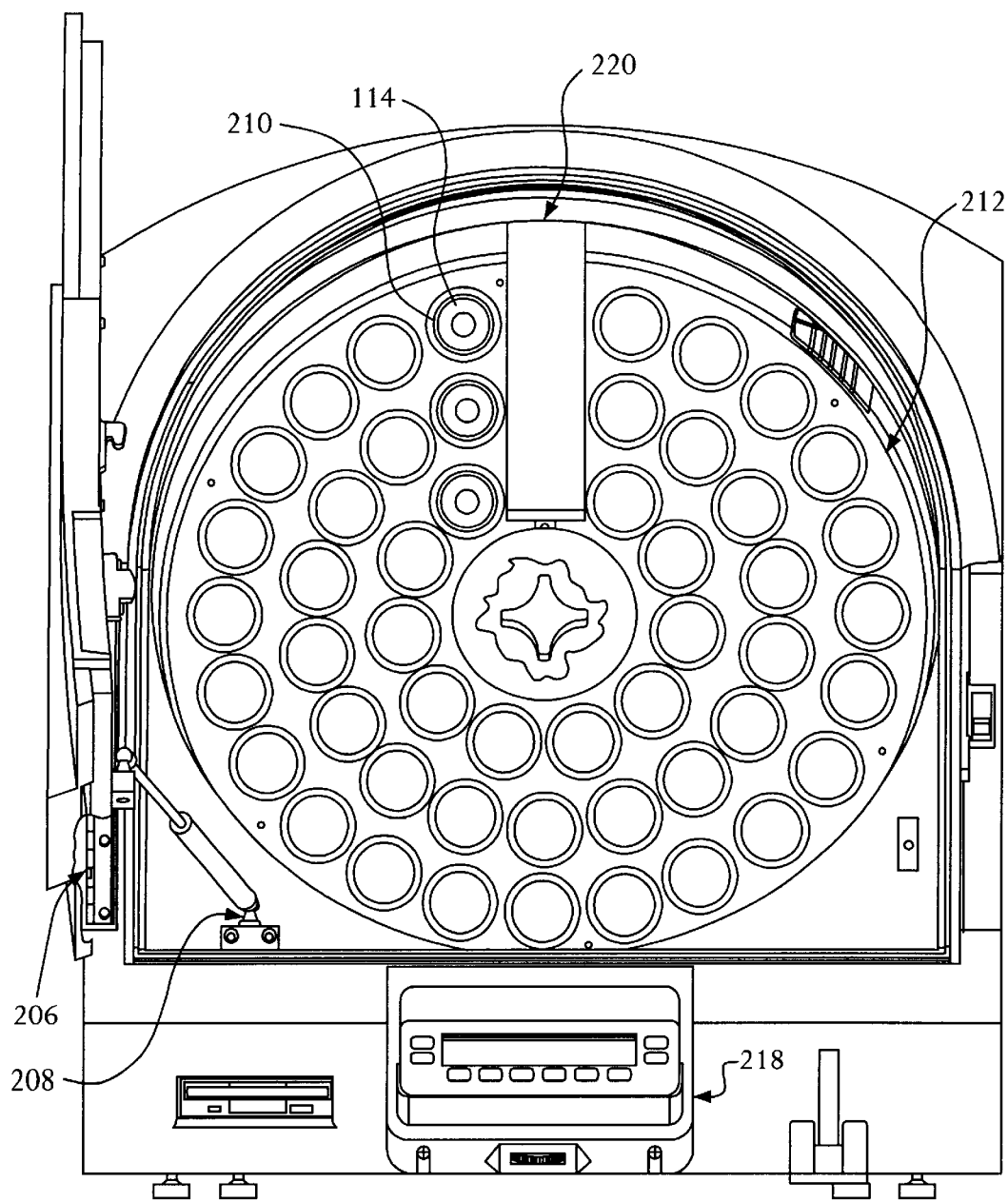
FIG. 14 is a front view of the instrument shown in FIG. 13.
Figure 15:
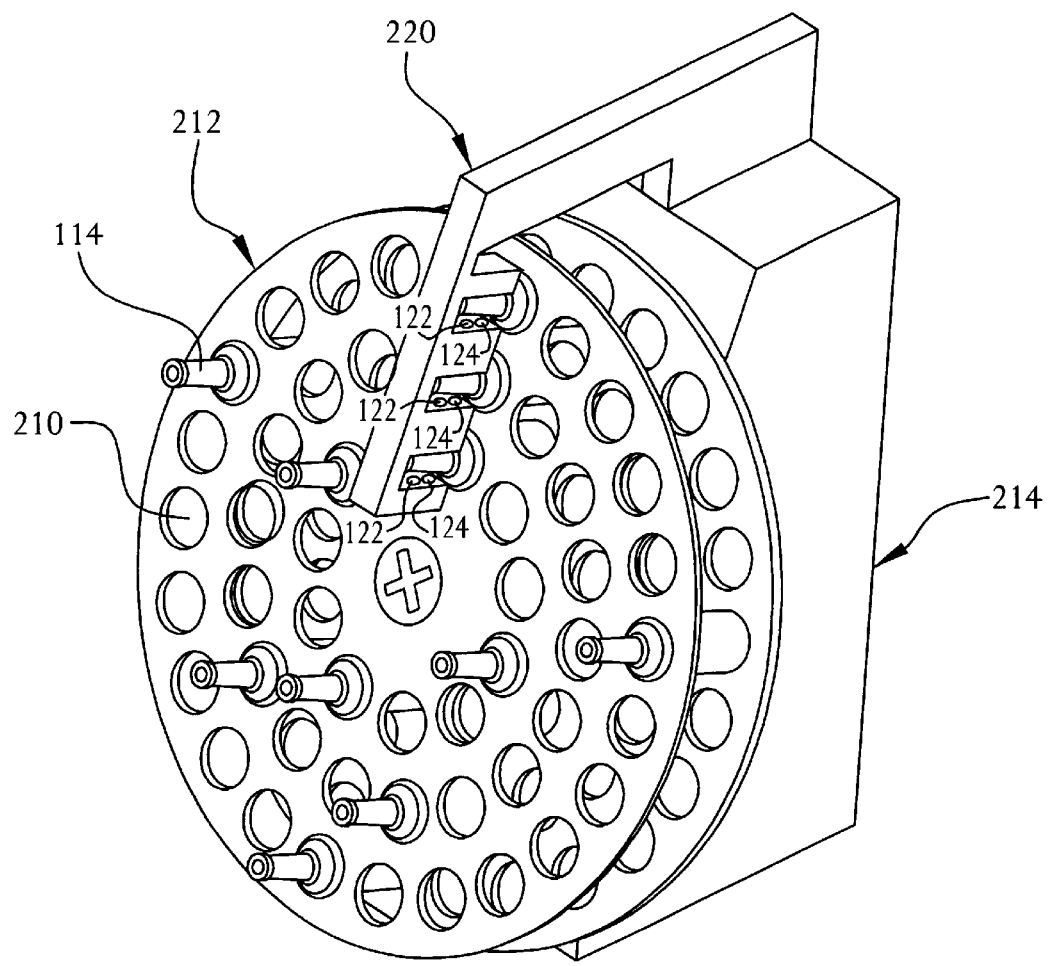
FIG. 15 is a detailed perspective view of the carousel and detector assembly arrangement in the instrument shown in FIGS. 13 and 14.

As shown in FIGS. 14–16, sample vials 114 are loaded into openings 210 of a carousel 212. The carousel 212 is rotatably mounted to a carousel mount 214, which are both housed in the interior chamber of the housing 202. The carousel is operable by a motor 216 under the control of a controller (not shown), such as the type of controller described above, to rotate in a clockwise or counter clockwise direction, as desired. The instrument 200 further includes a control panel 218 which enables an operator to set the parameters of the instrument 200, such as the incubation temperature, speed of rotation of the carousel 212, and so on.

As further shown in FIGS. 14–17, instrument 200 includes a stationary monitoring assembly 220 that is mounted to the carousel mount 214 and is used to monitor the samples in the sample vials 114 in the manner similar to that described above. However, instead of the monitoring assembly 220 moving with respect to the sample vials 114, the carousel 212 rotates the sample vials 114 past the respective sets of lasers 122 and 124 and detector 126 so that the lasers 122 and 124 can emit laser light as described above through the respective necks of the sample vials 114. The lasers 122, 124 and detector 126 are coupled to the type of circuitry shown, for example, in FIG. 9, and described above. Accordingly, as the carousel 212 is rotated to move the sample vials 114 past their respective lasers 122 and 124 and detector 126, the photothermal spectroscopy techniques described above are performed to monitor the concentration of a gas, such as oxygen or carbon dioxide, or the concentration of a liquid or solid, in the sample vial to thus detect for microorganism growth in the sample vial based on the monitored concentration.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for monitoring the concentration of a medium in at least one container, comprising:
    an energy emitting device, adapted to emit a first energy signal toward a location in said container, said first energy signal having a wavelength that is substantially equal to a wavelength at which said medium absorbs said first energy signal so that absorption of said first energy signal changes a refractive index of a portion of said medium or an adjoining medium;
    a second energy emitting device, adapted to emit a second energy signal toward said portion of said medium while said refractive index of said portion of said medium is changed by said first energy signal;
    a detector, adapted to detect a portion of said second energy signal that passes through said portion of said medium; and
    a signal analyzer, adapted to analyze said detected portion of said second energy signal to determine an amount of a sample in said container based on a concentration of said medium in said container, wherein
        said signal analyzer analyzes said detection portion of said second energy signal to determine whether said sample includes an organism which consumes or emits said medium.

2. A system for monitoring the concentration of a medium in at least one container, comprising:
    an energy emitting device, adapted to emit a first energy signal toward a location in said container, said first energy signal having a wavelength that is substantially equal to a wavelength at which said medium absorbs said first energy signal so that absorption of said first energy signal changes a refractive index of a portion of said medium or an adjoining medium;
    a second energy emitting device, adapted to emit a second energy signal toward said portion of said medium while said refractive index of said portion of said medium is changed by said first energy signal;
    a detector, adapted to detect a portion of said second energy signal that passes through said portion of said medium; and
    a housing, adapted to house said first and second energy emitting devices and said detector, said housing being movable to position said first and second energy emitting devices and said detector proximate to each of said containers at different moments in time so that said first and second energy emitting devices are adapted to emit their respective said first and second energy signals toward each said container and said detector is adapted to detect each respective said portion of each said respective second energy signal that passes through each said respective portion of said medium in each said respective container.

3. A system as claimed in claim 2, further comprising:
    a signal analyzer, adapted to analyze each said respective detected portion of said second energy signal to determine a respective amount of a respective sample in each said respective container based on a respective concentration of said respective medium in each said respective container.

4. A system as claimed in claim 2, wherein:
    said containers are arranged in a plurality of rows and columns; and
    said housing is adapted to move along said rows and columns of said containers.

5. A system as claimed in claim 2, wherein:
    said housing is adapted to extend said first and second energy emitting devices and said detector toward any said container and to retract said energy emitting device and said detector away from said any container.

6. A method for monitoring the concentration of a medium in at least one container, comprising:
    emitting a first energy signal toward a location in said container, said first energy signal having a wavelength that is substantially equal to a wavelength at which said medium absorbs said first energy signal so that absorption of said first energy signal changes a refractive index of a portion of said medium or an adjoining medium;
    emitting a second energy signal toward said portion of said medium or adjoining medium while said refractive index of said portion of said medium is changed by said first energy signal;
    detecting a portion of said second energy signal that passes through said portion of said medium; and
    analyzing said detected portion of said second energy signal to determine an amount of a sample in said container based on a concentration of said medium in said container, wherein
        said analyzing analyzes said detection portion of said second energy signal to determine whether said sample includes an organism which consumes or emits said medium.

7. A method for monitoring the concentration of a medium in at least one container, comprising:
    emitting a first energy signal toward a location in said container, said first energy signal having a wavelength that is substantially equal to a wavelength at which said medium absorbs said first energy signal so that absorption of said first energy signal changes a refractive index of a portion of said medium or an adjoining medium;

emitting a second energy signal toward said portion of said medium or adjoining medium while said refractive index of said portion of said medium is changed by said first energy signal;

detecting a portion of said second energy signal that passes through said portion of said medium or adjoining medium, emitting said first and second energy signals toward each of a plurality of said containers at respective moments in time; and detecting each respective said portion of each said respective second energy signal that passes through each said respective portion of said medium or adjoining medium in each said respective container at said respective moments in time.

8. A method as claimed in claim 7, further comprising:

analyzing each said respective detected portion of said second energy signal to determine a respective amount of a respective sample in each said respective container based on a respective concentration of said respective medium in each said respective container.

9. A method for monitoring the concentration of a medium in at least one container, comprising:

emitting a first energy signal toward a location in said container, said first energy signal having a wavelength that is substantially equal to a wavelength at which said medium absorbs said first energy signal so that absorption of said first energy signal changes a refractive index of a portion of said medium or an adjoining medium;

emitting a second energy signal toward said portion of said medium or adjoining medium while said refractive index of said portion of said medium is changed by said first energy signal;

detecting a portion of said second energy signal that passes through said portion of said medium or adjoining medium, a housing having plurality of openings therein, each of said openings being adapted to receive a respective container therein, said housing being movable to position each of said containers proximate to said first and second energy emitting devices and said detector at different moments in time so that said first and second energy emitting devices are adapted to emit their respective said first and second energy signals toward each said container and said detector is adapted to detect each respective said portion of each said respective second energy signal that passes through each said respective portion of said medium in each said respective container.

10. A system as claimed in claim 9, further comprising:

a signal analyzer, adapted to analyze each said respective detected portion of said second energy signal to determine a respective amount of a respective sample in each said respective container based on a respective concentration of said respective medium in each said respective container.

11. A system as claimed in claim 9, wherein:

said housing is substantially circular, and said openings are disposed circumferentially about said housing; and said housing is adapted to rotate to move said containers proximate to said first and second energy emitting devices and said detector.

12. A method for monitoring the concentration of a medium in at least one container, comprising:

emitting a first energy signal toward a location in said container, said first energy signal having a wavelength that is substantially equal to a wavelength at which said medium absorbs said first energy signal so that absorption of said first energy signal changes a refractive index of a portion of said medium or an adjoining medium;

emitting a second energy signal toward said portion of said medium or adjoining medium while said refractive index of said portion of said medium is changed by said first energy signal;

detecting a portion of said second energy signal that passes through said portion of said medium or adjoining medium, placing said containers in a housing having a plurality of openings therein, each of said openings being adapted to receive a respective container therein; and moving said housing to position each of said containers proximate to said first and second energy emitting devices and said detector at different moments in time so that said first and second energy emitting devices are adapted to emit their respective said first and second energy signals toward each said container and said detector is adapted to detect each respective said portion of each said respective second energy signal that passes through each said respective portion of said medium in each said respective container.

13. A method as claimed in claim 12, further comprising:

analyzing each said respective detected portion of said second energy signal to determine a respective amount of a respective sample in each said respective container based on a respective concentration of said respective medium in each said respective container.

14. A method as claimed in claim 12, wherein:

said housing is substantially circular, and said openings are disposed circumferentially about said housing; and said moving step rotates said housing to move said containers proximate to said first and second energy emitting devices and said detector.

* * * * *